United States Patent
Ganaja et al.

[11] Patent Number: 6,126,677
[45] Date of Patent: Oct. 3, 2000

[54] SUTURE FASTENER AND INSTRUMENT

[75] Inventors: Scott O. Ganaja, San Luis Obispo; Nicholas M. Grissafi, Rancho Santa Margarita; Paul J. White, San Clemente, all of Calif.

[73] Assignee: NoKnots Group Inc., Rancho Santa Margarita, Calif.

[21] Appl. No.: 08/892,931

[22] Filed: Jul. 15, 1997

Related U.S. Application Data

[63] Continuation-in-part of application No. 08/650,831, May 20, 1996, abandoned.

[51] Int. Cl.[7] .................................................. A61B 17/00
[52] U.S. Cl. ............................................................. 606/232
[58] Field of Search ........................... 606/232, 72, 151, 606/74; 411/34–39, 43, 184–189, 511

[56] References Cited

U.S. PATENT DOCUMENTS

| | | | |
|---|---|---|---|
| 2,379,676 | 7/1945 | Blackstone | 43/44.91 |
| 4,484,570 | 11/1984 | Sutter et al. | 606/72 |
| 4,644,681 | 2/1987 | Hutson | 43/44.91 |
| 5,078,731 | 1/1992 | Hayhurst | 606/232 |
| 5,258,015 | 11/1993 | Li et al. | 606/232 |
| 5,383,905 | 1/1995 | Golds et al. | 606/232 |
| 5,782,865 | 7/1998 | Grotz | 606/232 |

*Primary Examiner*—Michael Buiz
*Assistant Examiner*—Vikki Trinh
*Attorney, Agent, or Firm*—LaRiviere, Grubman & Payne, LLP

[57] ABSTRACT

A suture fastener includes male and female components being made of a bio dissolvable material. The male component has a flange extending transversely to its longitudinal axis at one end thereof. The female component has a hole defined therein for receiving the male component. The female component includes a surface extending transversely to the longitudinal axis of the hole, behind which the flange of the male component is retained upon insertion of the male component into the female component. A suture is clamped between the male and female components upon insertion of the male component into the female component. An instrument for inserting the male component into the female component is also disclosed.

19 Claims, 7 Drawing Sheets

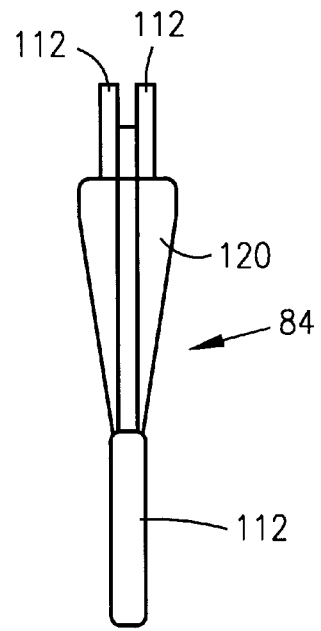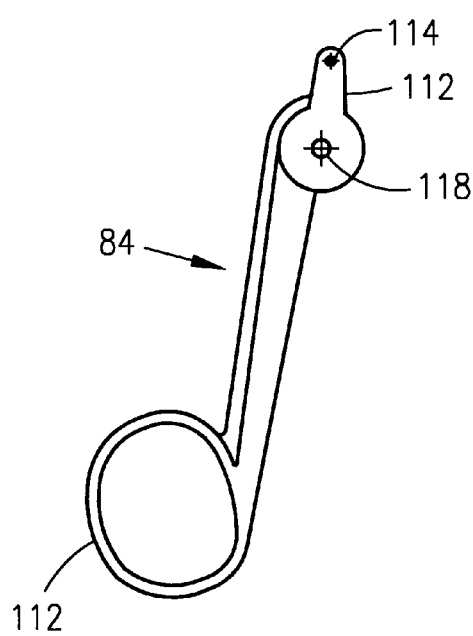
FIG. 8(a)    FIG. 8(b)
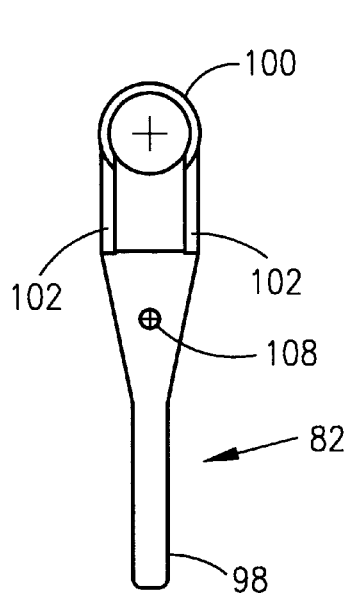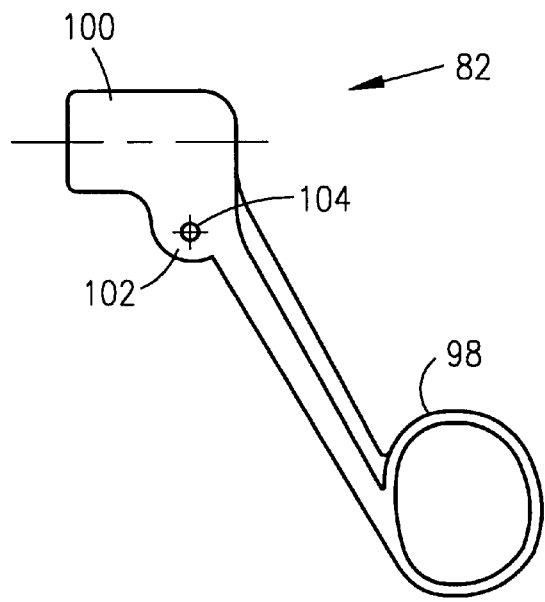
FIG. 9(a)    FIG. 9(b)

6,126,677

SUTURE FASTENER AND INSTRUMENT

RELATED APPLICATIONS

This is a continuation in part of patent application Ser. No. 08/650,831 filed on May 20, 1996, abandoned.

TECHNICAL FIELD

The present invention relates to a suture fastener and an instrument for applying the suture fastener to a suture.

BACKGROUND OF THE INVENTION

Current trends in surgery have been focused heavily on operating techniques which strive to be as non-invasive as possible. Small incisions are made in the patient, and specialized instruments, with small cutting heads and viewing devices are inserted into the patient to perform the necessary surgery. The problem is however that, if the tissue being operated on is to be sutured, it is very difficult to perform the suturing through the small incision which has been made in the patient. Accordingly, there is a need for a suture fastener and a suturing instrument which can be used in such minimally invasive surgery.

SUMMARY OF THE INVENTION

According to the invention there is provided a suture fastener comprising:

a male component being made of a bio dissolvable material and having a longitudinal axis, the male component including a projection extending transversely to the longitudinal axis; and a female component being made of a bio dissolvable material and having a surface defining a hole having a longitudinal axis, for receiving the male component, the surface further including a portion extending transversely to the longitudinal axis of the hole behind which the projection of the male component is retained upon insertion of the male component into the hole defined in the female component, a suture being clampable between the male and female components upon insertion of the male component into the female component.

Preferably, the male component has first and second ends, the projection is a flange defined at the first end of the male component, and there is a groove defined across the first end of the male component for receiving a portion of a suture to be fastened.

Further according to the invention there is provided a suture fastener comprising:

a male component having a longitudinal axis, the male component including first and second ends and a projection extending transversely to the longitudinal axis, the male component further having a tapered surface between the first and second ends; and a female component having a surface defining a tapered hole having a longitudinal axis, for receiving the male component, the surface further including a portion extending transversely to the longitudinal axis of the hole behind which the projection of the male component is retained upon insertion of the male component into the hole defined in the female component, a suture being clampable between the tapered surface of the male component and the surface of the female component upon insertion of the male component into the female component.

The invention also provides for an instrument for applying a suture fastener to a suture, the suture fastener comprising first and second interlocking components between which a suture is clampable, the instrument comprising:

a tube having an aperture defined therein for receiving a portion of a suture to which the suture fastener is to be applied;

first retaining means located in the tube on a first side of the aperture, the first retaining means for releasably retaining the first component of the suture fastener;

second retaining means located in the tube on a second side of the aperture, the second retaining means for releasably retaining the second component of the suture fastener; and actuating means for moving the second retaining means towards the first retaining means thereby to bring the first and second components of the suture fastener into engagement.

Other features of the invention are disclosed or apparent in the section entitled "BEST MODE OF CARRYING OUT THE INVENTION".

BRIEF DESCRIPTION OF THE DRAWINGS

For fuller understanding of the present invention, reference is made to the accompanying drawings in the following detailed description of the Best Mode of Carrying Out the Invention. In the drawings:

FIGS. 8a and 8b illustrate, in a plan view and a side view, the pivoting handle used in the instrument illustrated in FIG. 4;

FIGS. 9a and 9b illustrate, in a plan view and a side view, the fixed handle used in the instrument illustrated in FIG. 4;

BEST MODE OF CARRYING OUT THE INVENTION

As suturing techniques and devices are well known in the art, in order to avoid confusion, while enabling those skilled in the art to practice the claimed invention, this specification omits many details with respect to known items.

A suture fastener according to the invention comprises a male component and a female component which are configured to interlock and clamp a suture between them.

Figure 1B:
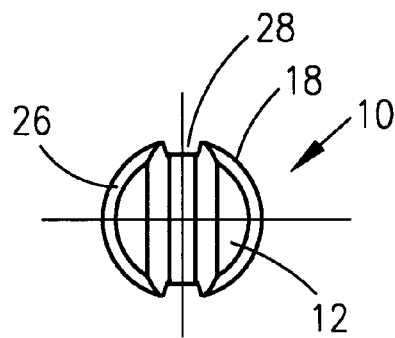
FIGS. 1a–1b illustrate, in four orthogonal views, a male component of a suture fastener in accordance with the invention.
Figure 1A:
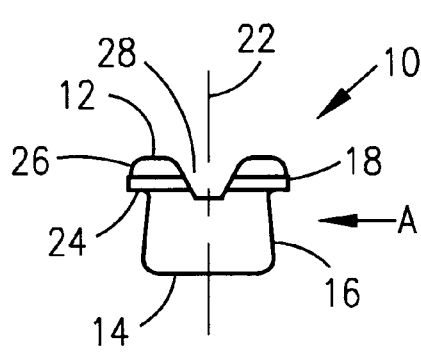
Figure 1C:
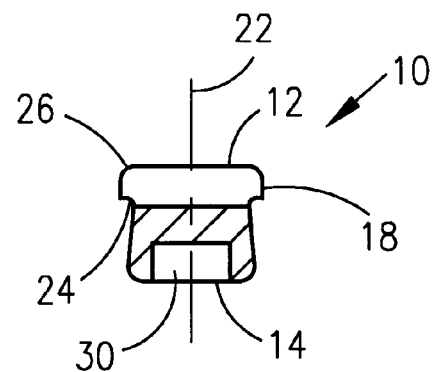
Figure 1D:
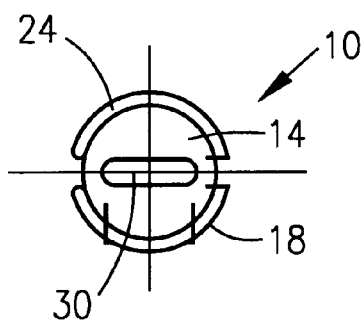

The male component, generally indicated by the numeral 10, is illustrated in a side view in FIG. 1(a), a top view in FIG. 1(*b*), a longitudinal cross sectional view in FIG. 1(*c*), and a bottom view in FIG. 1(*d*). The view in FIG. 1(*c*) is taken in direction A in FIG. 1(*a*).

The male component 10 has a first end 12 and a second end 14, and has a tapered surface 16 between the first and second ends 12, 14. The surface 16 tapers from the second end 14 towards the first end 12, and serves, together with a complementary tapered surface on the female component, to clamp a suture between the male component 10 and a female component, as will be discussed in more detail below. The tapered surface 16 also serves to prevent the male component 10 from slipping through the female component after insertion. The total angle of taper of the surface 16 measured between two opposed sides of the surface 16 is 10°.

The male component further comprises a projection in the form of a flange 18, which extends transversely to the longitudinal axis of the male component 10. The flange 18 has a lower surface 24 which, upon insertion of the male component 10 into a female component, locates against a corresponding surface in the female component, thereby to lock the male component 10 into place in the female component.

The flange 18 also has a rounded upper edge 26 which facilitates the insertion of the male component 10 into the female component.

The male component 10 has a groove 28 defined across the first end 12. The groove 28 serves two purposes. Firstly, the groove retains and locates a the suture in the correct position across the male component during suture fastening, as will be described in more detail below. Secondly, the groove divides the flange 18 into two halves, which can then flex towards another in a resilient and predictable manner upon insertion of the male 10 component into the female component.

To facilitate the mounting of the male component 10, the second side 14 has a recess 30 defined therein. The recess 30 is slot-shaped, and is sized to receive the prongs of a retaining clip as will be discussed in more detail below.

Figure 2B:
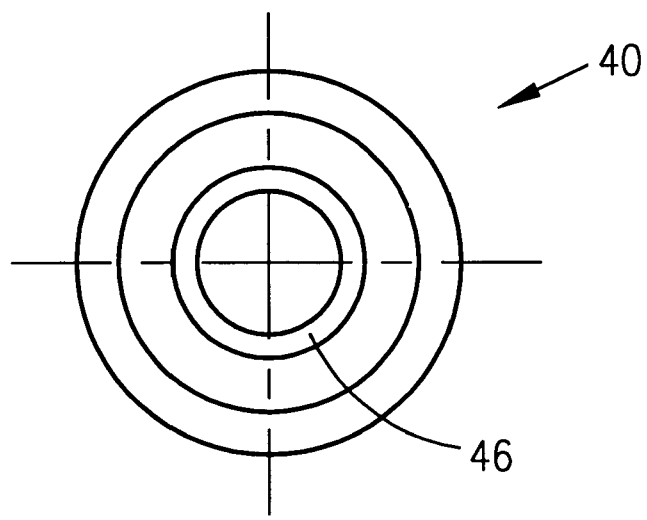
FIGS. 2a and 2b illustrate, in a top view and a longitudinal cross sectional view, a female component of a suture fastener in accordance with the invention.
Figure 2A:
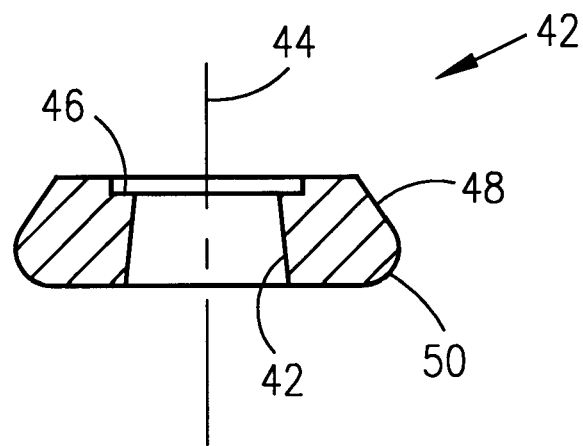

The female component, generally indicated by the numeral 40, is illustrated in a longitudinal cross sectional view in FIG. 2(*a*) and in a top view in FIG. 2(*b*). The female component 40 is generally ring shaped, with a hole therein for defined by an inner surface 42. The hole defined by the surface 42 is for receiving the male component as will be described in more detail below. The axis of the hole defined by the inner surface 42 is generally aligned with the longitudinal axis 44 of the female component, and defines a taper which is complementary to the taper of the surface 16. The total angle of taper of the inner surface 42 measured between two opposed sides of the surface 42 is 10°.

The inner surface 42 includes a shoulder 46 which extends transversely to the longitudinal axis 44 of the hole. The flange 18 of the male component 10 is retained behind the shoulder 46 upon insertion of the male component into the female component 40.

The outer surface of the female component 40 includes a generally frusto-conical portion 48 at the end of the female portion adjacent to the shoulder 46, and a rounded portion 50 at the other end of the female component 40. The frusto-conical portion 48 serves as a seating surface when the female component is mounted in the instrument which applies the suture fastener to a suture. The rounded portion 50 is engaged by a retaining spring in the instrument used to apply the suture fastener to a suture, as will be discussed in more detail below with reference to FIGS. 4 to 9.

Both the male component 10 and the female component 40 are made of a bio-dissolvable material which dissolves in the human body after an appropriate healing time has passed, in a manner well known in the surgical field. In the best mode embodiment of the invention, the components 10, 40 are made of poly-L-lactide dissolvable plastic. This material also provides the required degree of compliance and resilience which is required to permit the male component 10 to deform while being inserted into the female component 40, and to return to its original shape once the flange 18 has passed the shoulder 46.

Figure 3A:
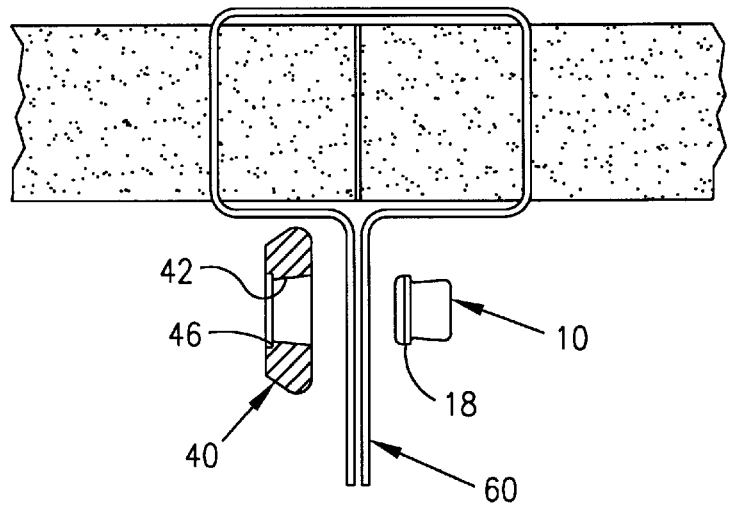
FIGS. 3a–3c illustrate a method of fastening a suture using the suture fastener of the invention.
Figure 3B:
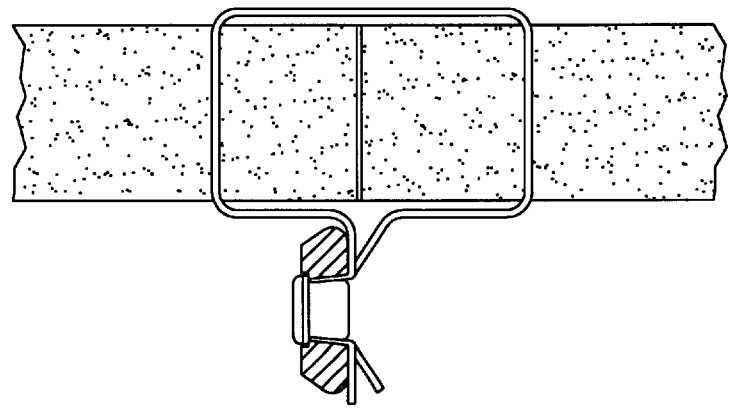
Figure 3C:
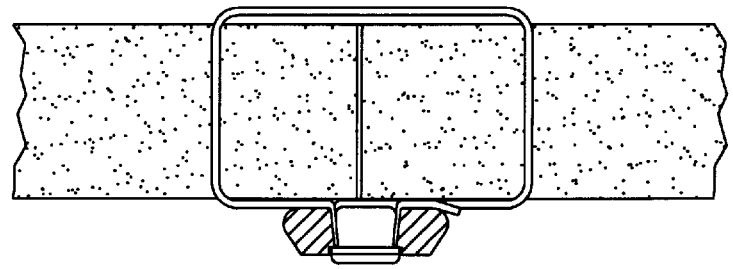

Referring now to FIGS. 3*a*–3*c* in conjunction with FIGS. 1 and 2, in use a suture 60 is applied to tissue 62 by a surgeon. The two ends of the suture 60 are brought together, and the male component 10 and the female component 40 are positioned on opposite sides of the suture 60 as shown in FIG. 3(*a*).

The male component 10 and the female component 40 are then brought together, with the suture being located in the groove 28 defined by the male component 10. As the male component 10 enters the female component 40, the two halves of the flange 18 deflect towards each other under the action of the inner surface 42 acting on the rounded upper edge 26 of the flange 18. The male component 10 is pushed into the female component 20 until the flange 18 passes the shoulder 46, at which time the two halves of the flange resume their original shape. The male component is now locked in place by the engagement of the lower surface 24 of the flange with the shoulder 46 of the female component. The suture now passes from the tissue 62, , across the first end 12 of the male component (i.e. through the groove 28), between the surface 42 and the surface 16 on the other side, and out of the suture fastener adjacent to the second end 14 of the male component. This is illustrated in FIG. 3(*b*).

The ends of the suture 60 are preferably trimmed automatically by the instrument which is used to apply the suture fastener 10, 40 to the suture 60, as will be described in more detail below with reference to FIGS. 4 to 9.

The suture is held clamped in place by the clamping action provided by an interference fit between the inner surface 42 of the female component 40, and the surface 16 of the male component 10. This clamping of the suture 60 is enhanced by the wedging action resulting from the relatively shallow taper of the inner surface 42 and the surface 16.

Figure 4:
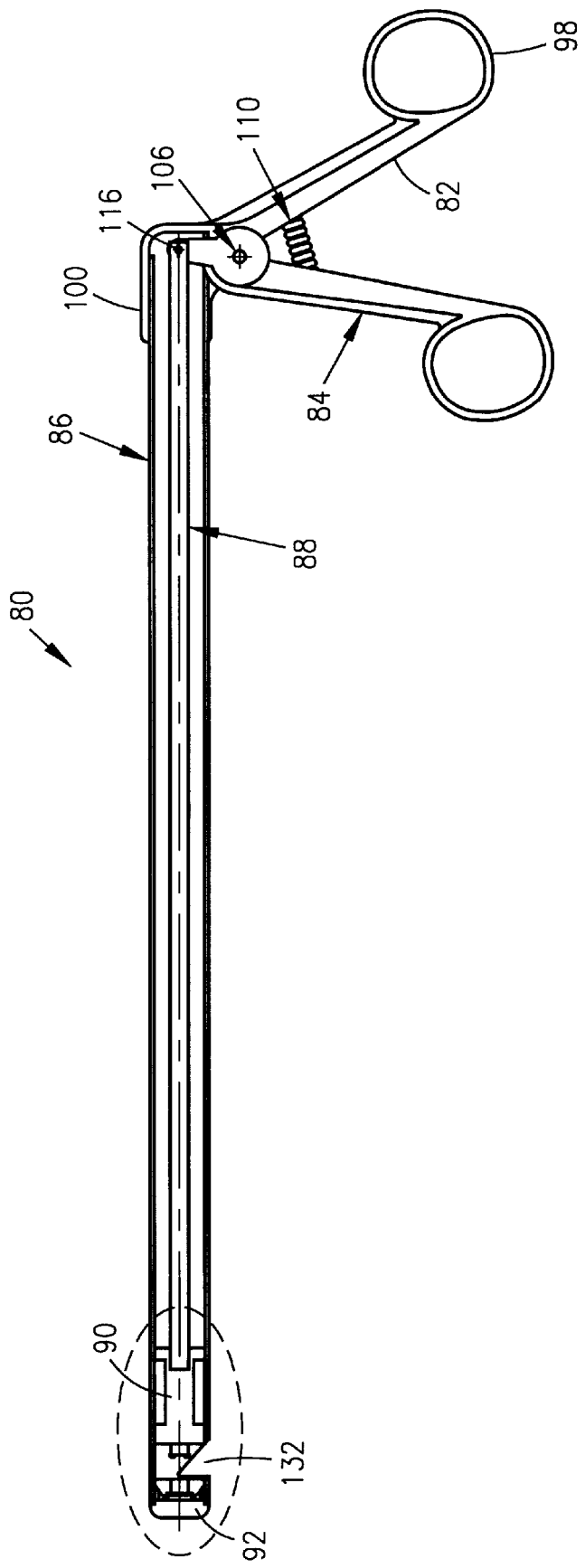
FIG. 4 is a partial longitudinal cross sectional view of an instrument for use in the method illustrated in FIG. 3.
Figure 5:
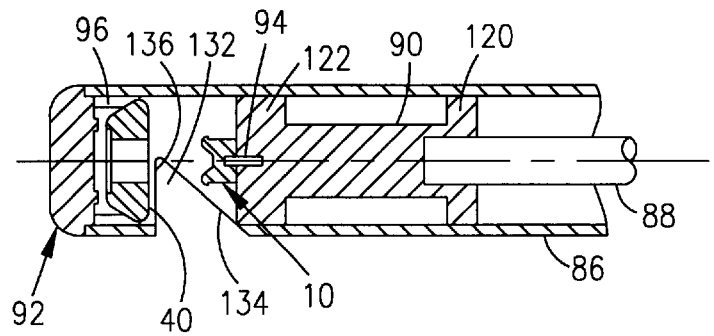
FIG. 5 is an enlarged view of the tip of the instrument illustrated in FIG. 4.

An instrument for applying the suture fastener to the suture is illustrated in a partial cross-sectional view in FIG. 4. An enlarged view of the circled portion in FIG. 4 is shown in FIG. 5.

The instrument, generally indicated by the numeral 80, comprises two handles, a fixed handle 82 and a pivoting handle 84, an elongated cylindrical tube 86, and actuating rod 88, a plunger 90, and end plug 92, a clip 94 and a spring 96.

The fixed handle 82, shown in plan and side view in FIGS. 9*a* and 9*b*, is preferably made of plastic but may be made of stainless steel, and has a finger loop 98 formed at one end thereof. The other end of the fixed handle 82 has a cylindrical sleeve 100 formed thereon, into which one end of the tube 86 is glued. The sleeve 100 is open along its lower side in the figure, to provide an entrance to the sleeve for the pivoting handle 84.

Depending from each side of the sleeve 100 is a skirt 102. Each skirt 102 defines a hole 104 which supports a pivot screw 106. The pivot screw 106 mounts the pivoting handle 84 for rotational movement with respect to the fixed handle 82. A further hole 108 is defined in the inner edge of the pivoting handle 82. The hole 108 is for receiving a compression spring 110 which in use biases the fixed and pivoting handles 82, 84 to an open position.

The pivoting handle 84, shown in plan and side view in FIGS. 8a and 8b, is preferably made of plastic but may be made of stainless steel, and also has a finger loop 112 formed at one end thereof. The other end of the pivoting handle 84 has two crank arms 114 formed thereon. Each crank arm 112 has a hole 114 defined therein. The holes 114 in use receive a pivot pin 116 for mounting one end of the actuating rod 88.

A cylindrical hole 118 is defined in a relatively thicker portion 120 of the pivoting handle 84. The cylindrical hole 118 and the pivoting pin 106 are for mounting the pivoting handle 84 for rotational movement with respect to the stationary handle 82. The relatively thicker portion 120 of the pivoting handle 84 is sized to fit between the two skirts 102 of the fixed handle 98 with a relatively snug clearance fit.

The actuating rod 88 is mounted at one end thereof to the pivoting pin 116, and at the other end thereof to the plunger 90. The actuating rod 88 is preferably cemented into a hole defined in the plunger 90, but it may also be secured in the hole by means of an interference fit. As will be appreciated from FIG. 4, the arrangement of the pivoting handle 84, the pivot pin 106, the pivot pin 116, and the actuating rod 88 provides a means whereby rotational movements of the pivoting handle 84 with respect to the fixed handle 82 advances or retracts to the actuating rod 88 in the cylindrical tube 86.

The plunger 90 has a flange 120 at one end thereof, and a flange 122 at the other end thereof. The flanges 120, 122 are for locating the plunger in the cylindrical tube 86, and are sized to permit sliding movement of the plunger 90 in the cylindrical tube 86.

A cylindrical hole 124 is defined in the one end of the plunger 90, for receiving one end of the actuating rod 88 in an interference relationship. A slot 126 is defined in the other end of the plunger 90, for receiving the clip 94.

It should be noted that the one edge 123 of the flange 122 is formed with a sharp edge, while the opposite edge 125 is rounded. This is done to trim the suture automatically in use of the instrument, as will be described on more detail below.

Figure 7A:
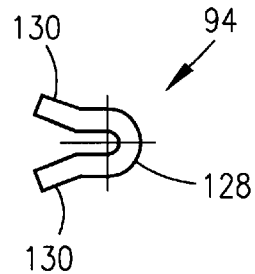
FIGS. 7a and 7b illustrate, in a plan view and an side view, the retaining clip used in the instrument illustrated in FIG. 4.
Figure 7B:
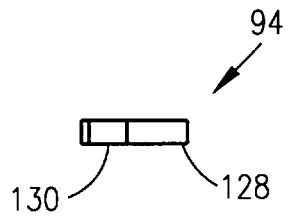
Figure 10B:
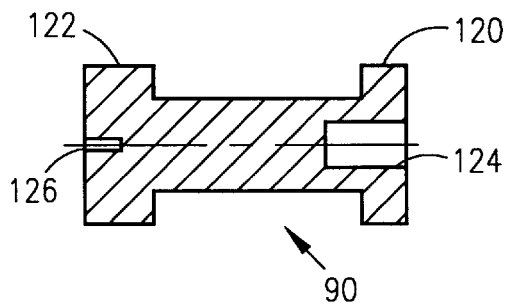
FIGS. 10a and 10b illustrate, in a plan view and a top view, the plunger used in the instrument illustrated in FIG. 4.
Figure 10A:
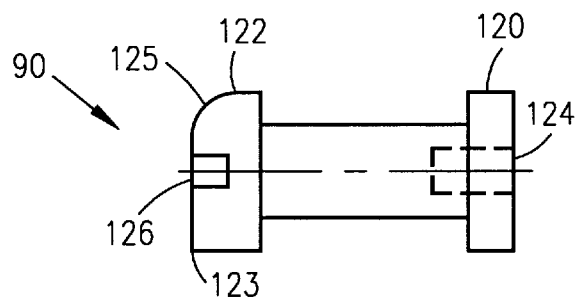

The clip 94, which is shown in plan and top view in FIGS. 7a and 7b, is made of a length of stainless steel wire bent to form a rounded portion 128 and two legs 130. The rounded portion 128 of the clip 94 is dimensioned to fit into the slot 126 of the plunger 90 in an interference fit relationship. The size and spacing of the legs 130 of the clip 94 are selected to provide a positive engagement between the ends of the legs 130 and the recess 30 defined in the second end 14 of the male component 12. In this manner, the male component 10 is mounted to the plunger 90 in use by means of the clip 94.

The cylindrical tube 86 is mounted into the sleeve 100 at its one end, and is closed at its other end by the end plug 92. The cylindrical tube 86 has a notch 132 defined therein between the plunger 90 and the end plug 92. The notch 132, is formed symmetrically about the cross sectional plane of FIG. 5 and is defined by an edge 134 which is at an acute angle to the longitudinal axis of the cylindrical tube 86, and by an edge 136 which is generally transverse to the longitudinal axis of the cylindrical tube 86.

It will be appreciated from FIG. 5 that the apices of the notch 132 are generally aligned with the groove 28 defined in the first end of the male component 10 when the male component 10 is mounted on the clip 94. Accordingly, if a suture is placed against the outer surface of the cylindrical tube 86 adjacent to the plunger 90, then is moved in the direction of the end plug 92, the suture will proceed along the angled edge 134 until it is positioned in the apices of the notch 132 across the cylindrical tube 86 between the male component 10 and the female component 40, and aligned with groove 28 formed in the male component 10.

Figure 11A:
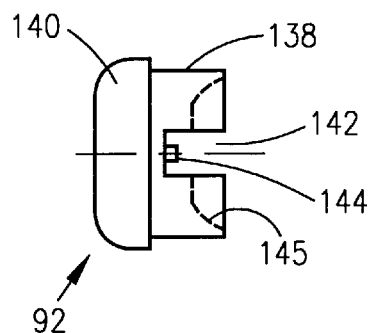
FIGS. 11a–11b illustrate, in three orthogonal views, the plug or end cap used in the instrument illustrated in FIG. 4.
Figure 11B:
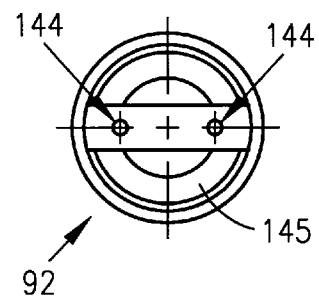
Figure 11C:
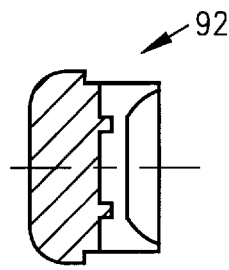

The end plug 92, which is shown in a side view, a top sectional view, and an end view in FIGS. 11a, 11b and 11c, is fitted into the end of the cylindrical tube 86. The end plug 92 is held in place by means of an interference fit between the outer surface 138 of the end plug 92 and the inner surface of the cylindrical tube 86. The end plug 92 is provided with a rounded cap portion 140 which is sized and shaped to prevent damage to adjacent tissue during use of the instrument 80.

The end plug 92 is provided with a slot 142 for receiving the retaining spring 96. The retaining spring 96 locates against the flat bottom surface of the slot 142, and is held in place by means of two posts 144 which locate in two holes defined in the retaining spring 96. The end plug 92 has a recess 145 defined therein which is shaped to receive the frusto-conical portion 48 of the female component 40. The recess 145 provides stable alignment and seating of the female component 40 in the instrument 80.

Figure 6A:
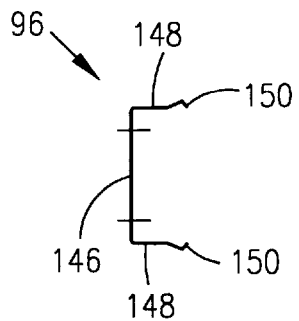
FIGS. 6a and 6b illustrate, in a plan and a side view, the retaining spring used in the instrument illustrated in FIG. 4.
Figure 6B:
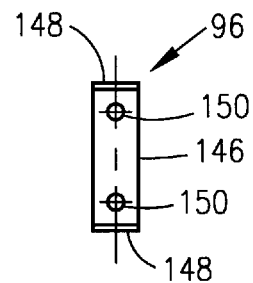

The retaining spring 96, which is shown in a plan and a side view in FIGS. 6a and 6b, is made of stainless steel, and comprises a base 146 and two arms 148. The base 146 has two holes 150 defined therein which are sized and spaced to receive the posts 144 of the end plug 92. The posts 144 of the end plug 92 are staked over the retaining spring 96 to hold the retaining spring 96 in place in the slot 142. The ends of the arms 148 have curved portions 150 which are shaped to receive and releasably engage the rounded portion 50 of the female component 40.

Referring now to all the figures, and in particular FIGS. 3a–3c, 4 and 5, the instrument 80 is loaded with a female component 40 seated in the end plug 92. The frusto-conical portion 48 of the female component 40 engages the surface defining the recess 145, and the female component is held in place by the curved portions 150 of the retaining clip 96 engaging the rounded portion 50 of the female component.

The instrument is also loaded with a male component 10, with the legs 130 of the clip 94 located in the recess 30. The orientation of the plunger 90 is such that, when the male component 10 is located on the clip 94, the groove 28 defined across the first end 12 of the male component is aligned with the two apices of the notch 132.

In this regard it should be noted that the instrument 80 is supplied to the surgical facility in a loaded condition. Due to the small size of the components 10, 40, and the often messy surgical environment, the instrument 80 is intended for single use, whereafter it will be disposed or recycled.

A surgeon, upon desiring to fasten the suture at the end of the surgical procedure, slips the two ends of the suture into the notch 132 in the cylindrical tube 86. This locates a portion of the suture between the male component 10 and the female component 40, aligned with the groove 28 in the male component 10.

The surgeon then squeezes the pivoting handle 84 towards the fixed handle 98 against the bias of the compression spring. This advances the actuating rod 88 and the plunger 90 along the cylindrical tube, which in turn presses the male component 10 and the suture into the female component 40, as described above with reference to FIGS. 3a–3c.

As the plunger 90 passes the edge 136 of the notch 132, the sharp edge 123 of the plunger 90 trims the ends of the suture adjacent to the suture fastener 10, 40 on the one side, while the rounded edge 125 of the plunger 90 ensures that the suture is not cut on the other side. The surgeon will of course have to make sure that the suture is inserted correctly into the notch 132, to ensure that the wrong side of the suture is not cut by the sharp edge 123. Alternatively, the plunger 90 could be provided with two rounded edges 125, so that the suture is not cut upon application of the suture fastener 10, 40 to a suture. In such a case, the trimming of the suture will be done separately.

The surgeon will then permit the handles 82 and 84 to return to their open position under the bias of the spring 110. This will cause the plunger 90 to withdraw from the notch 132 down the cylindrical tube 86, which will cause the male component and/or the female component to disengage from the retaining clip 94 and the retaining spring 96 respectively. If either the male component 10 or the female component 40 remains attached to the clip 94 or the spring 96 respectively, they will be gently pulled loose by the action of removing the suture from the notch 132.

The surgical instrument will then be discarded or recycled.

Thus it will be appreciated that the end plug 92 and the retaining spring 96 together form first retaining means located in the cylindrical tube 86 on a first side of the aperture or notch 132, which together releasably retain the female component 40, while the plunger 90 and the retaining clip 94 form second retaining means located in the cylindrical tube 86 on a second side of the aperture or notch 132, which together releasably retain the male component 10 of the suture fastener, and the handles 82 and 84 and the actuating rod 88 together form actuating means for moving the plunger 90 and the retaining clip 94 towards the end plug 92 and the retaining spring 96, thereby to bring the female and male components 40, 10 of the suture fastener into engagement.

It will be appreciated that many modifications can be made to the embodiments described above without departing from the spirit and the scope of the invention.

For example, the actuating means of the surgical instrument could be a paddle type of lever attached directly to the actuating rod 88 and running parallel to the tube 86 in a slot formed in the tube. Also, the tube 86 could be could be swaged or crimped at either the plug end and/or the handle end to attach the end plug 92 or the fixed handle 82 to the tube 86. Further, the plunger 90 could be formed with two curved edges so as to be non-cutting. Finally, the materials from which the various components are made could be selected from a number of suitable alternatives.

What is claimed is:

1. A suture fastener comprising:
    a male component being made of a bio dissolvable material, said male component having an outside surface defining an outer wall; and
    a female component being made of a bio dissolvable material and having a surface, the surface defining a hole for receiving the male component and a shoulder for coupling the male component, the hole having an inside wall, a suture being clampable between the outer wall of the male component and said inside wall of said hole in said female component upon insertion of the male component into the female component.

2. A suture fastener according to claim 1 wherein the outer wall of the male component has first and second ends, said first end having a flange for interlocking a with the shoulder of the female component.

3. A suture fastener according to claim 2 wherein said male component has a groove defined across the flange, said groove for receiving a portion of a suture to be fastened.

4. A suture fastener according to claim 2 wherein;
    the outer wall of the male component defines a taper between said first and second ends;
    the inside wall of said hole in said female component defining a taper corresponding to the taper of the outer wall of the male component; and
    the male and female components in assembled configuration providing an interference fit for clamping a portion of a suture between the outer wall of the male component and the inside wall of said hole of the female component.

5. A suture fastener according to claim 4 wherein:
    the taper of the outer wall of the male component is at an angle of about 10°; and
    the corresponding taper of the inside wall of said hole in said female component is at an angle of about 10°.

6. A suture fastener according to claim 2 wherein the second end of the male component comprises having a pocket.

7. A suture fastener according to claim 6 wherein said pocket is defined by a slot-shaped recess.

8. A suture fastener comprising:
    a male component having a first and a second end, said male component having an approximately cylindrical shape with an outside surface; and
    a generally ring shaped female component having a top surface and a bottom surface and a bore for receiving the male component, said bore having an inside surface, the top surface further including a shoulder portion behind which the first end of the male component is retained upon insertion of the first end of the male component into and through the bore from the bottom surface, a suture being clamped between the approximately cylindrical outside surface of the male component and the inside surface of the bore in the female component upon insertion of the male component into the female component.

9. A suture fastener according to claim 8, wherein:
    the male component defines a taper between the first and second ends of the outside surface of said cylindrical shape; and
    the inside surface of the bore in the female component defines a corresponding taper.

10. A suture fastener according to claim 8, wherein the first end of said male component defines a flange, the flange capable of engaging the top surface of the female component upon insertion of the flange into and through the bore from the bottom surface, to interlock said male component and female component.

11. A suture fastener according to claim 10, wherein there is a groove defined across the flange, said groove for receiving a portion of a suture to be fastened.

12. A suture fastener according to claim 8, wherein the second end of said male component defines a pocket.

13. A suture fastener according to claim 8, wherein the male component and the female component are formed from a bio dissolvable material.

14. A fastener for fastening two ends of a suture comprising:
    a male component and a female component configured to interlock and clamp two ends of a suture between them;
    said male component being made of a resilient material configured as a tapered member having a flange at one end, the flange being divided into two halves by a groove, the two halves of the flange being capable of being flexed towards one another in a resilient manner;

the female component being generally ring-shaped and having a central opening sized to receive the tapered member and having a shoulder on one side of the opening for engaging the flange of the male component, the flange of the male component being retained behind the shoulder of the female component when the components are interlocked together;

the male component and a female component being disposed on opposite sides of the two ends of the suture with the two ends of the suture being disposed in the groove so that the groove retains and locates the suture in a predetermined position across the male component; and the two ends of the suture being held in place by clamping action provided by an interference fit between the inner surface of the female component and the tapered member of the male component.

15. A suture fastener according to claim 14, wherein the male component and the female component are formed from a bio dissolvable material.

16. A suture fastener according to claim 15 wherein said bio dissolvable material is poly-L-lactide.

17. A fastener according to claim 14, wherein the end of said male component opposite the flange defines a pocket.

18. A fastener according to claim 17, wherein said pocket is a slot shaped recess.

19. A fastener according to claim 14 wherein:

the tapered member of the male component defining a taper of about 10°; and the inner surface of said central opening in said female component defining a corresponding taper of about 10°.

* * * * *